(12) United States Patent
Vinogradov et al.

(10) Patent No.: US 8,941,287 B2
(45) Date of Patent: Jan. 27, 2015

(54) METHOD AND DEVICE FOR LONG-TERM MONITORING OF COMPONENTS USING GUIDED WAVES

(75) Inventors: Sergey A. Vinogradov, San Antonio, TX (US); Hegeon Kwun, San Antonio, TX (US); Glenn M. Light, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 346 days.

(21) Appl. No.: 13/559,934

(22) Filed: Jul. 27, 2012

(65) Prior Publication Data
US 2014/0028154 A1    Jan. 30, 2014

(51) Int. Cl.
*B06B 1/06* (2006.01)

(52) U.S. Cl.
USPC ................................................. 310/336

(58) Field of Classification Search
CPC    H01L 41/0825; B06B 1/0644; B06B 1/0648; B06B 1/0651; B06B 1/0655; G01S 15/02
USPC .................................. 310/336–338
See application file for complete search history.

(56) References Cited

U.S. PATENT DOCUMENTS 7,573,261 B1    8/2009    Vinogradov
7,821,258 B2    10/2010    Vinogradov

OTHER PUBLICATIONS

Kwun, et al; "The Magnetostrictive Sensor Technology for Long Range Guided Wave Testing and Monitoring of Structures"; Materials Evaluation/Jan. 2003 (pp. 80-84).
Alleyne, et al; "Rapid Long-range Inspection of chemical Plant Pipework Using Guided Waves"; Guided Wave Inspection of Pipes; Insight vol. 43, No. 2, Feb. 2001 (pp. 93-96 and 101).

*Primary Examiner* — Derek Rosenau
(74) *Attorney, Agent, or Firm* — Grossman, Tucker et al

(57) ABSTRACT

The present disclosure relates to a system for monitoring a structural component. The system may include an electromechanical device to generate guided waves having a measurement surface and a bonding agent disposed on the measurement surface and configured to engage with the surface of the structural component. The system may also include a heating element for heating the measurement surface, the bonding agent, and capable of heating a portion of the structural component surface. In addition, the system may include a clamp for retaining the measurement surface relative to the structural component.

13 Claims, 4 Drawing Sheets ns for long term monitoring of components using guided waves and, in particular, methods and devices for maintaining the coupling between guided wave sensors and structural components.

BACKGROUND

Corrosion metal loss is one of many causes of structural damage. One method of rapidly surveying long lengths of structure components (such as pipes, tubes, cables, rods and plates) for flaws from a single test position includes the long-range guided-wave technique. The technique may be well suited for long-term (tens of years) of online, structural health monitoring applications with permanently installed guided wave probes. In order for this approach to work well, long-term stability of both the guided wave probe and the coupling means may be essential for maintaining consistent measurements.

Dry coupling often requires continuous pressure to be uniformly applied between the probe and the structural component. However, if the surface conditions are imperfect, uniform pressure may not provide sufficient uniform coupling. In addition, maintaining the same pressure becomes difficult in the presence of thermal cycling due to differential expansion of the pipe and fixtures sued to couple the guided wave into the pipe.

Various polymer systems, such as epoxy, polyurethane, or wax, have been used as couplants to bond the probe to the structural component. However, coupling is difficult to maintain due to various environmental conditions, such as thermal cycling or vibration. Field trials indicate that even seasonal temperature variations, in the range of 0° F. to 100° F., may cause debonding.

Shear wave coupling gel has also been used to couple the probes to structural components. However, maintaining a layer of a shear wave coupling gel may be difficult due to changes in the viscosity of the couplant that may occur over time. In addition, the effectiveness of shear wave coupling gel may also vary with operating temperature.

Once uncoupled, monitoring with the probe may be problematic. In addition, in many applications, the probe may be somewhat inaccessible making repairs difficult, such as when the probe is used to measure pipe buried in the ground or when the pipe is insulated. Further, costs associated with the labor and equipment related to replacing probes may make repairs difficult. Accordingly, a need remains to further develop systems for coupling guided wave probes to structural components for long term monitoring applications.

SUMMARY OF THE INVENTION

An aspect of the present disclosure relates to a system for monitoring a structural component. The system may include an electromechanical device to generate guided waves having a measurement surface and a bonding agent disposed on the measurement surface and configured to engage with the surface of the structural component. The system may also include a heating element for heating the bonding agent. In addition, the system may include a clamp for retaining the measurement surface relative to the structural component and the heating element relative to the bonding agent.

Another aspect of the present disclosure relates to a method of recoupling a structural component, particularly when the bonding agent is decoupled a) from the measurement surface, b) from the structural component surface, or c) from both the measurement surface and the structural component surface. The method may include providing contact pressure between a measurement surface of a guided wave probe, a surface of the structural component, and a bonding agent disposed between the measurement surface and the structural component surface. The method may also include heating the bonding agent with a heating element such that the bonding agent begins to flow and at least partially engaging the measurement surface and the structural component surface with the bonding agent. One may then re-solidify the bonding agent and couple the guided wave probe to the structural component.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

The present disclosure relates generally to methods and devices for long term monitoring of components using guided waves and, in particular, methods and devices for coupling and maintaining coupling between guided wave probes and structural components. Long-range guided-wave monitoring is an inspection method for rapidly surveying long lengths of structural components, such as pipes, tubes, cables, rods and plates, for flaws from a single test position. In long-term structural health monitoring, for example, guided wave probes may be permanently installed on a structural component and baseline data collected. Additional guided wave data may then be periodically collected with the guided wave probe. The periodically collected data may be compared to the baseline data. When defects are formed in the structure and grow, they alter the guided wave data obtained with the permanently installed guided wave sensors. By comparing the baseline data and the periodically acquired data, the changes in structural conditions that occur over time, such as defect initiation and growth may be tracked accurately for safe operation of the structure and prevention of unexpected structural failure.

Figure 1:
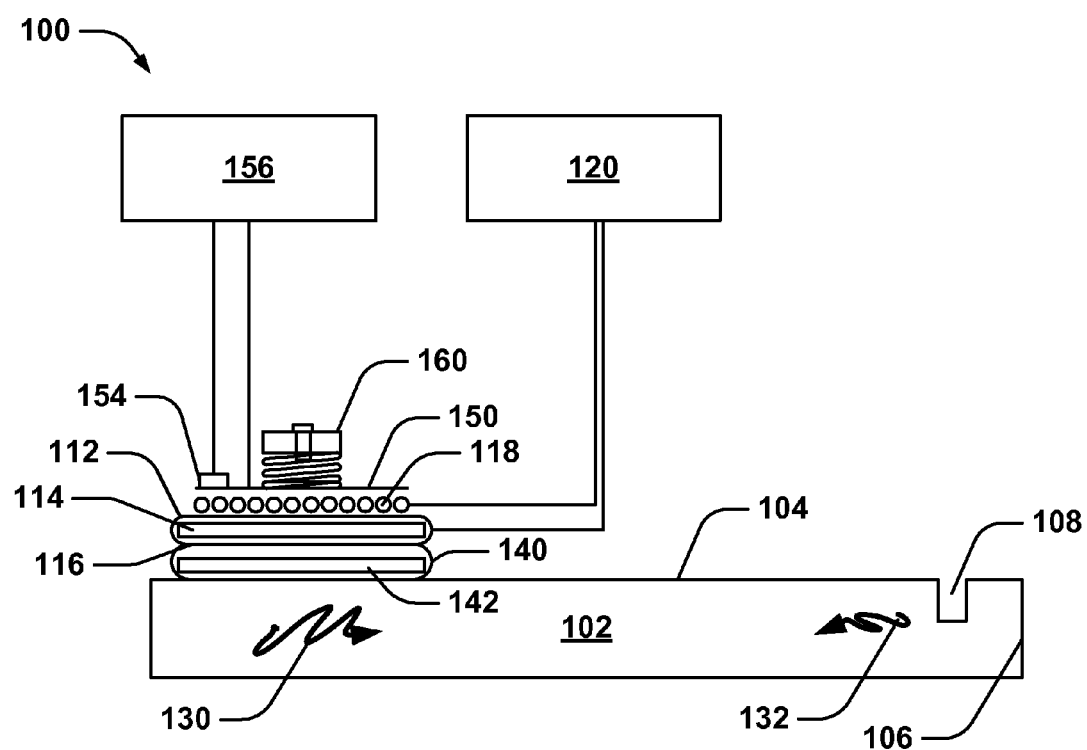
FIG. 1 illustrates a system for re-coupling a guided wave probe to a structural component.

FIG. 1 illustrates an example of a system 100 for monitoring structural components 102 and coupling a guided wave probe 112 to a structural component 102. Structural components 102 may be understood as components that form a given structure or increase or improve properties of a given structure such a tensile strength, compressive strength or flexural strength. Structural components 102 may include, for example, pipes, tubes, cables, rods and plates. In some instances, the structural components 102 may be tied to, integrated into, or embedded within a structure. The component 102 may include pipes for transporting substances over long or short distances, such as oil, gas, steam, reactants, resin, etc.; reinforcing bars for concrete; or steel beams employed in construction.

A guided wave probe 112 may be positioned adjacent to a surface 104 of the component 102. Specifically, guided waves 130, 132 may be generated in structural components 102 using the guided wave probe 112. The guided wave probe 112 may include electromechanical devices 114 including piezoelectric sensors, magnetostrictive sensors, electromagnetic acoustic transducers, or mechanical vibrators for inducing guided waves 130 in the component 102. The electromechanical devices 114 may include circuitry 118, such as coil windings. The electromechanical device 114 may also include a measurement surface 116, which may be struck by reflected guided waves 132.

After initial waves 130 are propagated through the component 102 the waves 130 reflect off an end of the component 106 as well as off any anomalies 108, such as voids, pits or disparities. The reflected waves 132 that impinge on the measurement surface 116 are detected by the electromechanical sensor 114 and converted into voltage changes. Guided wave probe instrumentation 120 may also be provided that processes or analyzes the voltage changes to draw inferences from attenuation of the waves and parameters such as an average signal amplitude at a given location, an average signal amplitude over a gated range, a root mean square value of the waveform or combinations thereof. Corrosion, for example, may increase the attenuation of the reflected waves and new anomalies may create new reflections.

To maintain consistency in measuring the reflected guided waves 132 over a period of time, it becomes relatively important to maintain consistency in the coupling state of the guided wave probe 112 to the structural component 102. In addition, more accurate readings may be obtained by reducing any disparities or voids between the couplant and the guided wave probe and/or the structural component. Therefore, as understood herein, coupling preferably encompasses not just contact between the couplant 140 and the probe 112 or structural component 102, but also bonding due to mechanical interlocking of the couplant 140 with the structural component 102 caused by the filling of at least a portion of the voids and or disparities between the couplant 140 and the probe measurement surface 116 or the structural surface 104. In that regard, it is preferred to provide a couplant that can ensure that waves produced by the guided wave probe 112 and which pass through the couplant 140 do so in a manner that is continuously efficient over time in the sense that there are little or no changes in pulse signals (initial or detected) that are unrelated to the structure 102 being analyzed.

In the present disclosure, the guided wave probe 112 may be coupled to the component 102 of interest through the use of bonding agent as a couplant 140. The bonding agent 140 may be any material that is capable of repeatedly softening upon the application of heat and/or pressure and re-hardening when cooled to provide or reestablish coupling between the guided wave probe and the structure to be analyzed such that guided wave inspection may proceed. Such guided wave inspection may also preferably occur under a non-pressure dependent condition.

The bonding agent may preferably comprise a polymeric bonding agent 140 which itself may preferably be a wax (e.g. a polyolefin having a MW of 4000-10,000 g/mole) or a thermoplastic resin and may include materials such as beeswax, poly(ethylene-co-vinylacetate), polyvinyl acetate, polyethylene including low density and high density polyethylene, polypropylene, and styrene block co-polymers including styrene-butadiene rubber, carnauba wax, paraffin wax, polyethylene wax, polypropylene wax, tetrafluoroethylene wax, shellac and pitch. The polymerinc bonding agent may also include polyamide type polymers.

The couplant 140 comprised of a polymeric bonding agent may preferably exhibit a melting point (° C.) in the range of 65.0° C. to 250.0° C., including all values and ranges therein. The melting point may be understood as the temperature at which a solid changes state from solid to liquid as measured by differential scanning calorimetry at a rate of 10° C./min. In some examples, the polymeric bonding agent 140 may exhibit a molecular weight of 4,000 g/mol or greater and up to 500,000 g/mol, including all values and increments therein, such as in the range of 4,000 g/mol to 100,000 g/mol when a relatively softer more malleable material is desired, or in the range of 100,000 g/mol to 500,000 g/mol when a relatively harder material is desired.

The polymeric bonding agent 140 may be applied to the probe 112 before installation or during installation. For example, the polymeric bonding agent 140 may be delivered in the form of a liquid or solid. The polymeric bonding agent 140 may be melted prior to it application to the probe 112 and/or the structural component 102. The polymeric bonding agent 140 may have a thickness in the range of 0.1 mm to 5.0 mm.

A coupling membrane 142 may also be positioned between the measurement surface 116 of the guided wave probe 112 and the structural component 102. The coupling membrane 142 may be at least partially encapsulated by the polymeric bonding agent 140 or partially infused with the polymeric bonding agent 140. The coupling membrane 142 may also be relatively stiff or relatively flexible and may be formed of woven or nonwoven fabrics or woven or nonwoven mesh. The coupling membrane 142 may include para-aramid fibers such as KEVLAR™, available from DuPont; fiber glass; carbon fiber, etc. The coupling membrane 142 may have a thickness in the range of (0.2 mm-3.0 mm).

A heating element 150 may be incorporated into the system to heat the polymeric binding agent 140 as well as the structural component 102 and the measurement surface 116 of the guided wave probe 112. The heating element 150 may include a resistive heating element in the form of a plate, coil, bands, etc., wherein the form of the heating element may be selected based on the geometry of the structural component 102. As illustrated, the heating element 150 preferably can directly contact the guided wave probe 112 and indirectly heats the polymer bonding agent 140 and a portion of the structural component 102 beneath the guided wave probe 112. However, the heating element may also be positioned between the guided wave probe and the polymeric bonding agent or between the structural component and the polymeric bonding agent. Furthermore, the heating element may be incorporated into the surface of the structural component.

Figure 2:
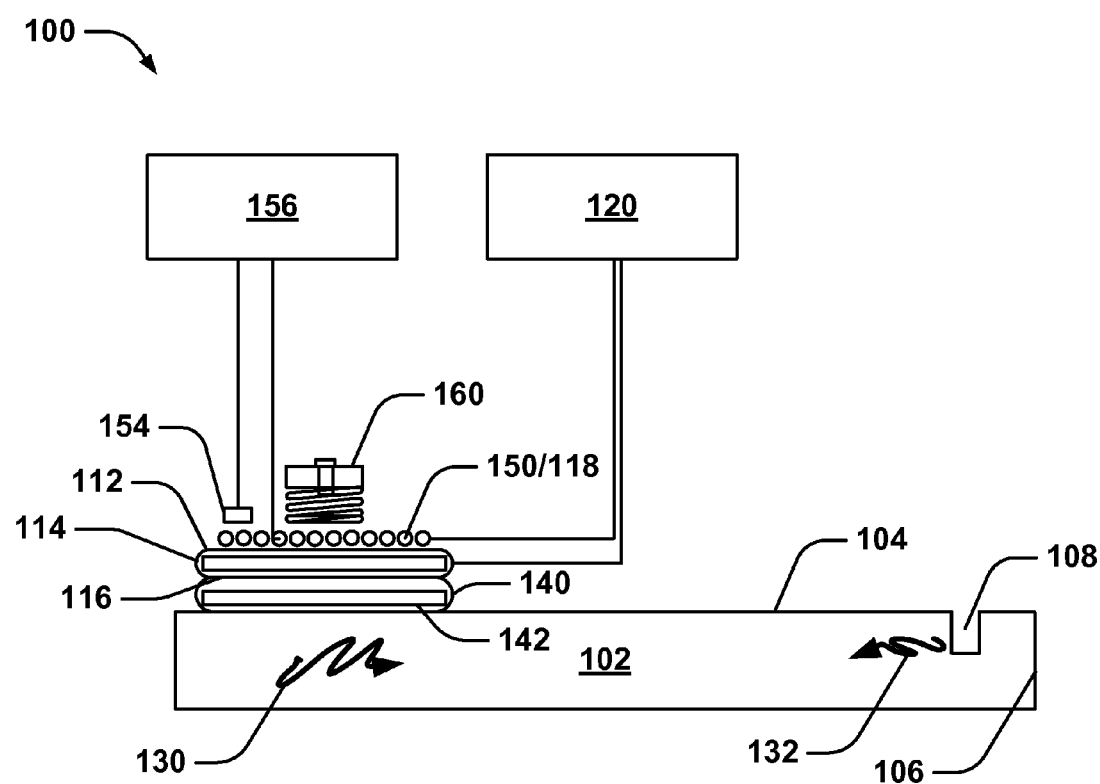
FIG. 2 illustrates a system for re-coupling a guided wave probe to a structural component.
Figure 3:
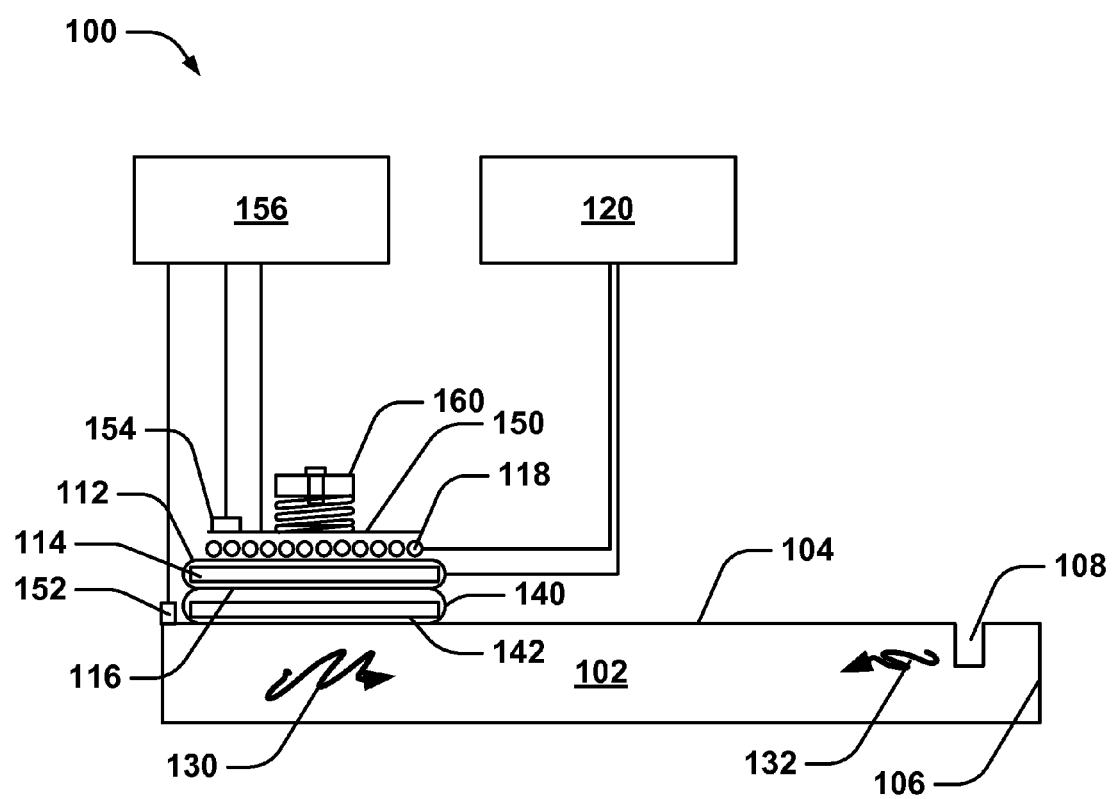
FIG. 3 illustrates a system for re-coupling a guided wave probe to a structural component.

As illustrated in FIG. 2, the heating element 150 may be part of the guided wave probe and may, for example, be formed by the circuitry and/or windings 118 of magnetostrictive guided wave probes. The heating element may again heat, not only the measurement surface 116 of the guided wave probe 112, but also a portion of the structural component that is disposed beneath the polymeric binding agent. Additional heating elements 152 may also be provided on the structural component 102 as illustrated in FIG. 3.

One or more temperature sensors 154 and a temperature control unit 156 may be provided to control the heating element 150. A temperature sensor 154 may be mounted on the measurement surface 116 of the guided wave probe, on the surface 104 of the structural component 102, or in both locations on the measurement surface 116 of the guided wave probe and on the surface 104 of the structural component 102. The temperature sensor may also be positioned near the coupling membrane 142, which may prevent over heating of the coupling membrane. The temperature control unit 156 may utilize the feedback from the temperature sensor(s) 154 to regulate the output of the heating element 150. In some embodiments, the temperature control unit 156 may regulate the output of the heating element 150 based on time with or without reference to a temperature sensor.

A clamping device 160 may be utilized to hold the guided wave probe 112 and the polymeric bonding agent 140 to the structural component 102. The clamp 160 may also hold or position the heating element 150 relative to the probe measuring surface 116 and/or the structural component 102. In addition, the clamp 160 may apply pressure to the guided wave probe 112 and the polymeric bonding agent 140 against structural component of 70 kPa or less, such as in the range of 1 kPa to 70 kPa, 10 kPa to 60 kPa, etc. Clamping devices may include band clamps such as V-band clamps, U-type clamps, T-bolt clamps, C-clamps, or other clamps. In some embodiments, the clamp 160 may include a spring that acts against the heating element 150 biasing the heating element 150 against the guided wave probe 112 and polymeric bonding agent 140.

The above system may be of particular use in coupling a structural component to a guided wave probe that has become decoupled over time, such as due to thermal cycling or vibrations. When initially assembling the system and coupling the guided wave probe 112 to the structural component 102 the polymeric bonding agent 140 may be applied directly to either the guided wave probe 112 or to the structural component. As alluded to above, the polymeric bonding agent 140 may be applied in liquid form as a hot-melt adhesive, or in solid form by transfer tape including a pressure sensitive adhesive carried on a liner. After applying the polymeric bonding agent 140, the guided wave probe 112 may be affixed to the surface 104 of the structural component 102. Specifically, the polymeric bonding agent 140 may wet the surfaces 116, 104 of the guided wave probe and structural component, respectively. Upon solidification of the polymeric bonding agent, the surfaces may be coupled together. That is, the polymeric bonding agent 140 may fill in any disparities in the measurement surface 116 and the structural component surface 104 and fill any voids between the surfaces. Therefore, voids or gaps between the measurement surface 116 and structural component surface 104 may be substantially and repeatedly eliminated.

If a separate heating element 150 is used, the heating element 150 may then be positioned, such as over the guided wave probe 112 as illustrated in FIG. 1. Finally, the clamp 160 may be positioned over the heating element 150, guided wave probe 112, polymeric binder 140 and the structural component 102 and adjusted to the appropriate pressure. In other embodiments, the polymeric bonding agent 140, guided wave probe 112, heating element 150 and clamp 160 may be pre-assembled and positioned over the structural component 102 at the same time.

Decoupling of the guided wave probe 112 from the structural component 104 may cause significant deviations in the measured reflected guided waves reducing the accuracy of the measurements. In other words, over time, the polymeric bonding agent may undergo physical changes (e.g. development of voids or debonding from the probe or structural component) which leads to a decoupling of the polymeric binding agent from the measurement surface of the guide wave probe and/or the structural component surface to be analyzed. Such decoupling may increase the width of the initial pulse detected by the guided wave probe, increase background noise and reduce the detected amplitude of reflected waves. This may hinder the ability to resolve the amplitude of the detected guided waves and possibly prevent the detection of smaller reflections.

In the event of decoupling, the system may now recouple the components back together. The guided wave instrument 120 may indicate to the temperature control unit 156 that a heating cycle should be initiated. Or, in some embodiments, a heating cycle may be initiated on a periodic basis by the temperature control unit 156, independent of what is detected by the guided wave instrument 120. Accordingly, when the guided wave probe 112 decouples from the heating element 150 and voids or disparities become present between the polymeric bonding agent 140 and the guided wave probe 112, the structural component 102, or both the guided wave probe 112 and the structural component 102, the system herein may now be used to couple the guided wave probe 112 and structural component 102 back together.

Contact pressure between the guided wave probe 112, and in particular the measurement surface 116 of the guided wave probe 112 and a surface 104 of the structural component 102 may be maintained by the clamp 160. The polymeric bonding agent 140 may be heated with the heating element 150 such that the polymeric bonding agent 140 begins to flow. That is, the viscosity of the polymeric bonding agent may begin to decrease allowing the polymeric bonding agent to engage the measurement surface of the guided wave probe and the structural component filling the disparities and voids that may have developed.

Heat may be applied with the heating element 150 for a given time period, when a given temperature detected by the temperature sensor(s) has been reached, or when a given temperature (as detected by the temperature sensor(s)) has been sustained for a specified time period, and then turned off. The given time period for which heat may be applied or sustained may preferably be in the range of one minute to 60 minutes, including all values and increments therein, such as 10 to 20 minutes, 20 to 30 minutes, 30 to 40 minutes, etc. The length of time may depend on the polymeric bonding agent selected and its associated melting characteristics. In addition, the bonding temperature, i.e., the temperature which the temperature sensor(s) detect, may preferably be in the range of 65.0° C. to 250.0° C., including all values and increments therein. The polymeric bonding agent may then re-solidify and couple the guided wave probe to the structural component.

In some embodiments, the guided wave instrument 120 may refrain from acquiring data during the coupling process. For example, the guided wave instrument 120 may refrain from acquiring data when the heating element 150 is active. Further, the temperature control unit 156 may indicate to the guided wave instrument 120 to proceed with measurements after it is estimated that the polymeric bonding agent has re-solidified. That is, the temperature control unit 156 may determine that the guided wave probe or the structural component has reached a second temperature (lower than the heating temperature) and, in some instances, that the second temperature has been sustained for a given time period. Furthermore, it may be desirable to activate the guided wave probe during the coupling process (either while heating or during re-solidification) to improve engagement of the surfaces of the guided wave probe and structural component, even if data is not acquired.

It is also possible to monitor the structural component during the re-coupling process. That is, the structural component may be monitored simultaneously with heating or re-solidifying the polymeric bonding agent. This is possible even when the heating element is integrated into the guided wave probe and the circuitry of the guided wave probe (i.e., the coil windings) are utilized as a resistance heater.

EXAMPLES

The following examples are presented for illustrative purposes only and therefore are not meant to limit the scope of the disclosure and claimed subject matter attached herein.

Figure 4:
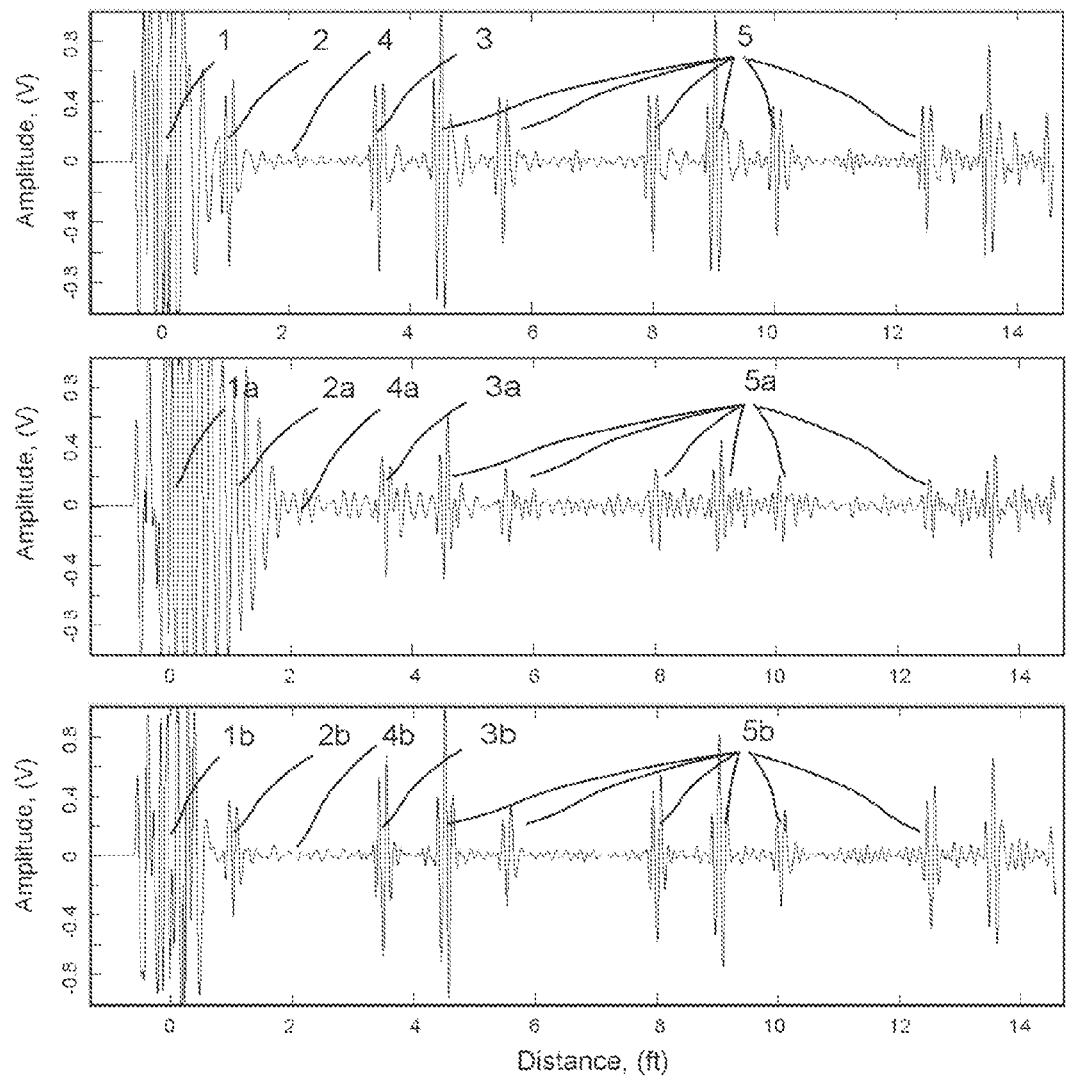
FIG. 4 illustrates a graph of data acquired for guided wave probe measurements after the initial coupling of the structural component to the guided wave probe, after decoupling occurs and after re-coupling of the guided wave probe to the structural component.

FIG. 4 includes data obtained from monitoring a 4 inch, schedule 40 pipe sample using wax to couple the guided wave probe to the pipe. The entire probe was heated together with local area of the component underneath the guided wave probe to the melting temperature of the wax. In the present example, it took about 30 minutes using a 40 Watt heater to bond the probe to the pipe. Once re-coupling was complete and the wax re-solidified, the guided wave instrument activated the guided wave probe to propagate guided waves in the structure and produce reflections.

The upper graph includes data acquired after the probe was initially coupled to the pipe and prior to decoupling. The middle graph includes data acquired after the probe decoupled from the pipe. The lower graph includes data acquired after the probe was re-coupled to the pipe. With reference to the upper graph, the amplitude and the width of the following signals can be clearly seen in FIG. 4: the initial pulse (1), responses from the near (2) and far end (3) of the pipe sample, background noise (4), and multiple reflection signals (5). Decoupling was induced by hammering on the pipe. After decoupling illustrated in the middle graph, the width of the initial pulse (1a) significantly changed, exhibiting relatively higher amplitudes over the width of the pulse. Also, the amplitude of all of the other signals (2a, 3a and 5a) were reduced and the background noise (4a) increased. After re-coupling the probe to the component surface, the width and amplitude of the initial pulse (1b) became similar to the amplitude (1) of the initial coupling state and the amplitude of the other signals (2a, 3a, and 5a) recovered. Furthermore, the background noise (4b) was reduced close to the initial levels (4).

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A system for monitoring a structural component having a surface, comprising:
   an electromechanical device having a measurement surface, wherein the electromechanical device generates guided waves;
   a bonding agent disposed on said measurement surface and configured to engage with the surface of said structural component, engage with the surface of said structural component, wherein said bonding agent will soften upon application of heat and harden with cooling to provide coupling between said electromechanical device and said structural component;
   a heating element for heating and softening said bonding agent;
   a clamp for retaining said measurement surface relative to the structural component and the heating element relative to the bonding agent.

2. The system of claim 1, wherein said electromechanical device is selected from the group consisting of a piezoelectric sensor, a magnetostrictive sensor, an electromagnetic acoustic transducer, and a mechanical vibrator.

3. The system of claim 1, wherein said bonding agent is a polymeric bonding agent.

4. The system of claim 1, wherein said bonding agent exhibits a melting temperature in the range of 65.0° C. to 250.0° C.

5. The system of claim 1, wherein said bonding agent is selected from the group consisting of carnauba wax, paraffin wax, polyethylene wax, polypropylene wax, tetrafluoroethylene wax, polyamide, shellac and pitch.

6. The system of claim 1, further comprising a coupling membrane at least partially encapsulated by said bonding agent.

7. The system of claim 1, further comprising a coupling membrane at least partially infused with said bonding agent.

8. The system of claim 7, wherein said coupling membrane is mesh.

9. The system of claim 7, wherein said coupling membrane includes fiberglass, carbon fiber, or kevlar.

10. The system of claim 1, wherein said electromechanical device is a magnetostrictive sensor including at least one crossed winding circuit and said heating element is said crossed winding circuit.

11. The system of claim 1, wherein said clamp retains said measurement surface against said structural component at a pressure of 1 kPa to 70 kPa.

12. The system of claim 3 wherein said polymeric bonding agent has a MW of 4000 to 500,000 g/mole.

13. The system of claim 1 wherein said heating element heats a portion of said measurement surface and a portion of said structural component surface.

* * * * *